(12) United States Patent
Wexler et al.

(10) Patent No.: US 6,201,990 B1
(45) Date of Patent: Mar. 13, 2001

(54) ELECTRICAL IMPEDANCE TOMOGRAPHY METHOD

(75) Inventors: Alvin Wexler, Winnipeg; Zhen Mu, Nepean, both of (CA)

(73) Assignee: Tasc Ltd., Winnepeg (CA)

( * ) Notice: Subject to any disclaimer, the term of this patent is extended or adjusted under 35 U.S.C. 154(b) by 0 days.

(21) Appl. No.: 08/943,131

(22) Filed: Oct. 3, 1997

(30) Foreign Application Priority Data

Oct. 2, 1997 (CA) .................................................. 2217603

(51) Int. Cl.[7] .................................................. A61B 5/053
(52) U.S. Cl. ............................ 600/547; 324/326; 324/357
(58) Field of Search ..................... 600/547; 324/323–326, 324/347, 354, 357, 600

(56) References Cited

U.S. PATENT DOCUMENTS

| | | | |
|---|---|---|---|
| 5,272,624 | * 12/1993 | Gisser et al. | 600/547 |
| 5,284,142 | * 2/1994 | Goble et al. | 600/547 |
| 5,465,730 | * 11/1995 | Zadehkoochak et al. | 600/547 |
| 5,544,662 | * 8/1996 | Saulnier et al. | 600/547 |
| 5,626,146 | * 5/1997 | Barber et al. | 600/547 |
| 5,807,251 | * 9/1998 | Wang et al. | 600/547 |
| 5,919,142 | * 7/1999 | Boone et al. | 600/547 |

* cited by examiner

*Primary Examiner*—Ruth S. Smith
(74) *Attorney, Agent, or Firm*—Pascal & Associates

(57) ABSTRACT

A method of imaging an object contained in a medium, having a specific impedance which is different from the specific impedance of the medium, comprising applying current to the medium at various locations at a surface of the medium, extracting current at other locations, detecting voltages produced by the current which has passed through the medium from the surface of the medium at various other locations, successively determining a location and shape and conductivity of the object with increasing accuracy by processing values of the detected voltages, determining a region in the medium in which the object is located from values of the detected voltages which are within upper and lower threshold values, applying acceleration procedures to the conductivities within the region in the course of iterative refinement of these values in the course of an imaging procedure, subsequently restricting further determination of the location of the object with increasing accuracy to voltages obtained from the region of the medium in which the object is located, and displaying an image on an axis using the restricted location determination values.

2 Claims, 8 Drawing Sheets

5 ITERATIONS FOR
PEAK DETECTION METHOD

20 ITERATIONS FOR
ORIGINAL ALGORITHM

5 ITERATIONS FOR
PEAK DETECTION METHOD

20 ITERATIONS FOR ORIGINAL ALGORITHM

5 ITERATIONS FOR PEAK DETECTION METHOD

ORIGINAL IMAGE CONTRAST [1:2]

20 ITERATIONS WITH
ORIGINAL ALGORITHM

MODEL

| | 2.00 |
| | 1.95 |
| | 1.90 |
| | 1.85 |
| | 1.80 |
| | 1.75 |
| | 1.70 |
| | 1.65 |
| | 1.60 |
| | 1.55 |
| | 1.50 |
| | 1.45 |
| | 1.40 |
| | 1.35 |
| | 1.30 |
| | 1.25 |
| | 1.20 |
| | 1.15 |
| | 1.10 |
| | 0.95 |

RESULT

| PHYSICAL ARRANGEMENT | IDEAL RECOVERED IMAGE | ACTUAL RECOVERED IMAGE |

ELECTRICAL IMPEDANCE TOMOGRAPHY METHOD

FIELD OF THE INVENTION

This invention relates to improved methods of detecting and locating an object contained in a medium which object has contrasting electrical conductivity and/or specific impedance compared to the medium.

BACKGROUND TO THE INVENTION

It was reported in 1926 by H. Fricke and S. Morse in the article "The electric capacity of tumours of the breast", (1926) J. Cancer Res. 16, pp. 310–376 that the electrical properties of breast tumors differ significantly from healthy tissue. Until now it has not been possible to use these properties to detect breast tumors in a manner useful in a clinical setting. However, some laboratory and imaging techniques have evolved.

Electrical Impedance Tomography (EIT) is an imaging methodology that is based upon electrical conductivity or impedance contrasts within the human body. EIT has been the subject of considerable attention recently but, generally, methods used for image recovery have yielded only low-resolution results.

U.S. Pat. No. 4,539,640, issued Sep. 3, 1995, to inventors Bradley Fry and Alvin Wexler (referred to below as the Wexler et al patent), and the article by A. Wexler, B. Fry and M.R. Neuman, entitled "Impedance-Computed Tomography: Algorithm And System", Applied Optics, Vol. 24, No. 23, pp. 3985–3992, describe a method and embodiment of a system that solved electromagnetic field equations that govern current flow in a conductive medium, and concurrently extracted an image of the interior of the medium based on the electric current conductivity (and, more generally, specific impedance) distribution in the medium. This provided a methodology for the correct mathematical solution of the inverse (imaging) problem and construction of electronic equipment for this purpose. The method also provided for the accommodation of a great number of pixels through the use of sparse-matrix techniques. U.S. Pat. No. 4,539,640 is incorporated herein by reference.

This methodology embodies a number of technological features, e.g. uses a well-conditioned, least-squares method, uses true three-dimensional field solving for images and conductivity values and for identification of characteristic pathologies, is applicable to complex impedance as well as to purely conductive imaging, it allows for application of known CT-based reconstruction methodologies and image processing operations between iterations, only simple contact of electrodes to the skin or to geophysical or other surfaces is sufficient to provide for contact and spreading resistance, it results in a sparse-matrix formulation for high-definition imaging, parallel data acquisition may be performed through frequency multiplexing for speed, and parallel image reconstruction may conveniently be accommodated.

EIT uncovers objects within a host medium by solving for resistivity (or, more generally, specific impedance) distributions within the body. Various techniques have previously been used that treat the flow of applied electrical currents as though they behave in a manner similar to X-ray beams. With this assumption, algebraic reconstruction techniques (ART) originally described by Gordon, Bender and Herman in the article "Algebraic Reconstruction Techniques (ART) For Three Dimensional Electron Microscopy and X-Ray Photography", (1970), J. Theor. Biol. 29, pp 471–481, have been employed by others to uncover a crude approximation of the EIT image.

ART finds wide and accurate use in applications of computed tomography other than EIT. Because electrical currents between any two electrodes flow throughout the body and do not follow ray-like paths, a straightforward application of ART is inappropriate. Therefore, as confirmed by R. H. T. Bates, G. C. McKinnon and A. Seager in the article "A Limitation On Systems For Imaging Electrical Conductivity Distributions", (1980), IEEE Biomed Eng. BME-27, pp. 418, a comprehensive field-solving approach is needed as part of the EIT imaging process.

A considerable body of EIT work has been done at the University of Sheffield in the U. K. Smith, Freeston and Brown describe their Applied Potential Tomography (APT) system which uses a weighted back-projection technique, in "A Real-Time Electrical Impedance Tomography System For Clinical Use—Design And Preliminary Results", (1995), IEEE Trans. Biomed. Eng. BME-42, pp. 133–140.

Guardo et al describe a back-projection reconstruction method which could detect a 3 ml plastic sphere at the centre of a torso-sized cylinder of saline, in "An Experimental Study In Electrical Impedance Tomography Using Back-projection Reconstruction", (1991), IEEE Trans. Biomed. Eng. 38 (7), pp. 617–627. This translates to approximately a 1.5 cm sphere in a 50 cm cylinder.

Shahidi, Guardo and Savard in "Electrical Impedance Tomography: Computational Analysis Based On Finite Element Models Of The Human Thorax With Cylindrical And Realistic Geometries", (1995), Annals Biomed. Eng. 23 (1), pp. 61–69, report that three-dimensional finite element method simulation results show that "a 10 ml edema region with a conductivity equal to that of blood can be detected at a 40 dB signal-to-noise ratio (SNR)", and further: "Detection of a smaller volume, in the order of 2 ml, should be possible by improving either the instrumentation to achieve 60 dB SNR or the performance of the reconstruction methods". These results, scaled to the size of the breast, indicate that even small breast tumors (less than 4 mm in diameter) should detectably alter surface potentials.

It should be noted that detection is not image reconstruction but it is a necessary precondition. Guardo's research team has demonstrated that a practical, measurable signal is available for use in EIT.

Henderson and Webster presented a means for displaying isoadmittance contours of the chest, Tasto and Schomberg described an impedance imaging technique that considers curved current flux tubes and uses back-projection techniques, Lytle and Dines report on the use of impedance techniques for geophysics applications and Price further discusses medical applications and techniques (Henderson, R. and Webster, J. (1978) "An Impedance Camera For Spatially Specific Measurements Of The Thorax", IEEE Trans. Biomech. Eng. BME-25, pp. 250; Tasto, M. and Schomberg, H. (1981) "Method Of And Device for Determining Internal Body Structure", Washington, D.C., U.S. Pat. No. 4,263,920; Lytle, R. J. and Dines, K. A. (1978) "An Impedance Camera: A System for Determining the Spatial Variation of Electrical Conductivity", (1978) Livermore, Calif.: Lawrence Livermore Laboratory Report UCRL-52413; and Price, L. R. (1979) "Electrical Impedance Computed Tomography (ICT): New Imaging Technique", IEEE Trans. Nucl. Sci. NS-26, 2736.

An alternative method as described in the aforenoted U.S. Pat. No. 4,539,640, involves the application of currents to the body and successive measurement of surface potentials.

This image recovery method involves the solution of the Poisson/Laplace equation while employing sparse-matrix techniques.

Dijkstra, A. M., B. H. Brown, A. D. Leathard, N. D. Harris, D. C. Barber, and D. L. Edbrooke "Review: Clinical Applications Of Electrical Impedance Tomography", (1993), J. Med. Eng. Technol. 17 (3), pp. 89–98 discuss clinical applications of EIT. They review the conductivity of tissues at around 50 kHz, and show the large contrasts that exist. In their view, " . . . the major disadvantage is the poor spatial resolution which is only about 10% of the diameter of the body. It seems likely that this may be improved to 5% (1 cm in a body of 20 cm diameter) and at this point it begins to be similar to that offered by a gamma camera. We should therefore regard the technique as a monitor of body function and not as an anatomical imaging method."

We believe that this conclusion is pessimistic, as the present invention provides a practical EIT method and apparatus with high resolution that can be used in a clinical setting.

SUMMARY OF THE INVENTION

In accordance with an embodiment of the present invention, we have developed methods to vastly improve the quality of edge detection at interfaces between surrounding (e.g. breast) tissues and small included objects (e.g. tumors), to accurately and rapidly image small objects and to substantially increase the speed of image extraction. It is believed that this provides a practical method and means that can be used for detection of breast tumors in a clinical setting.

It is known that breast tumor metastasis rapidly increases with tumor size. It has been shown that if all breast tumors are detected and removed by the time they reach 4 mm diameter, total metastasis would be 0.6%, indicating a 99.4% cure rate. We therefore also believe that an effective and relatively inexpensive EIT machine built in accordance with the principles of the present invention, used as a screening tool to find such tumors, could make breast cancer a highly curable disease.

The principles of the present invention can also be used for subterranean imaging, for the purposes of detection of contamination of groundwater, for location of landmines and other explosives (including those that are plastic encased), etc.

It is believed that by the use of the present invention, imaging of objects that are 5% of body diameter in size are achievable now and it is expected that the method can be used to image objects that are 2.5% of body diameter or smaller. This translates to breast tumors of 5 mm and 2.5 mm respectively. We believe that our new method will provide sufficient spatial resolution to detect tumors smaller than those typically found via mammography.

It is expected that use of the present improved methods for the imaging of objects located within bodies in EIT scanners for medical applications will be preferred because they are noninvasive and can be produced relatively inexpensively, as compared to X-ray CT (CAT scan) and MRI (magnetic resonance imaging), and may be operated by trained technicians. For geophysical applications, EIT scanners using the principles of the present invention provide an alternative to test boring and will be able to identify landfill site leachates prior to contamination of groundwater resources. It is believed that they can also be used to image plastic-coated land mines, which otherwise are very hard to find.

In accordance with an embodiment of the present invention, a method of imaging an object contained in a medium, having a conductivity which is different from the conductivity of the medium, comprises the steps of applying current to the medium at various locations at a surface of the medium, extracting current at various locations, detecting voltages due to currents which have passed through the medium from the surface of the medium at various other locations, successively determining the location and shape of the object with increasing accuracy by processing values of the detected voltages, and determining a region of the medium in which the object is located from values of the detected voltages.

Instead of processing for current values, the method can process for impedance, either resistive or complex.

BRIEF DESCRIPTION OF THE DRAWINGS

A better understanding of the invention will be obtained by a consideration of the detailed description below, in conjunction with the following drawings, in which.

DETAILED DESCRIPTION OF THE PREFERRED EMBODIMENTS

Figure 1:
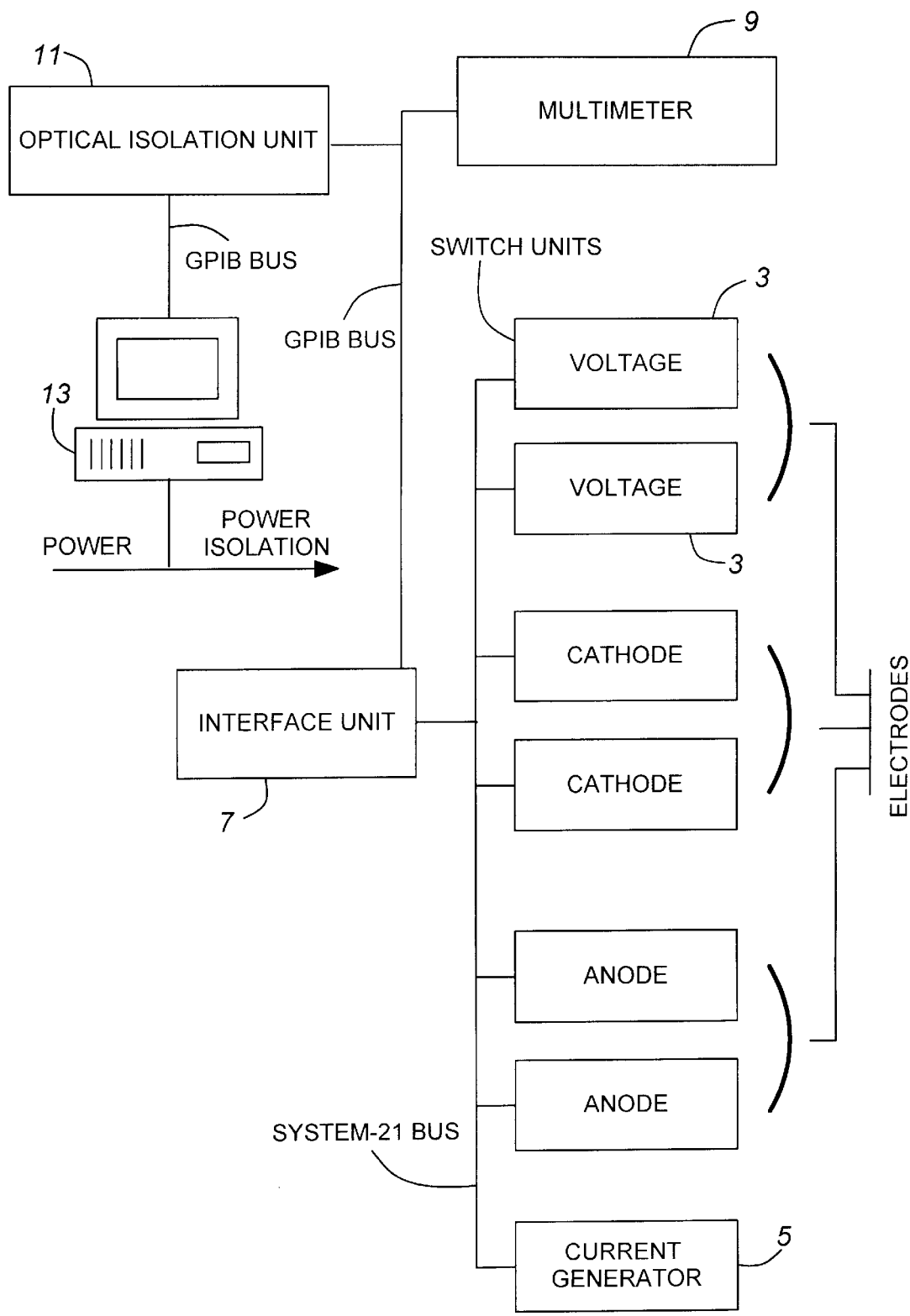
FIG. 1 is a block diagram of a system which can be used to implement the present invention.

FIG. 1 shows a block diagram of a system on which the present invention can be implemented.

The system is comprised of a set of electronic devices controlled by a personal computer. Communication was effected via an IEEE-488 parallel bus to Fluke/Philips proprietary System 21 units using a Philips GPIB Interface card installed on the computer. The interface card could address up to 14 GPIB instruments and was hardware and software configured to select an appropriate IRQ setting, DMA channel, and base I/O address.

Plural electrodes 1 for electrically contacting the surface of a medium such as the human body, the earth, etc., are formed into a matrix, and are connected to corresponding electrode selection switches 3. Pairs of electrodes form cathodes and anodes. The electrodes forming the matrix are disposed along preferably (but not essentially) mutual orthogonal axes x and y. A current generator 5 generates current in any effective waveform, which is applied to predetermined ones of the cathodes or anodes. The matrix is disposed in a position to overlay a surface of a medium to be analyzed, and to apply and receive current to and from the medium.

The switches 3 also switch the electrodes, to the input of an interface unit 7 which performs analog to digital conversion. The output of the interface unit is connected to a digital multimeter 9, which determines the amplitude of current and voltage received from the respective electrodes. The switch units preferably switch each electrode, to which current is not being applied, in a time-shared manner, to the meter through the interface unit.

In this manner, current is applied to plural places on the surface of the medium, and current is received from other plural places on the surface of the medium after passing through the medium. The interface converts the current to digital form, and is measured with the voltage by multimeter 9.

In a successful embodiment, six banks of twenty switches were used. The switch-banks were grouped in pairs based on their function during the monitoring, e.g. two pair for electrode selection, and a pair for measurement electrode selection. Each electrode served one of the three roles during a single measurement, and many electrodes served in all roles for a complete set of measurements. All units, except the multimeter, were controlled by a master switch unit interfacing between the IEEE bus and the System 21 bus. A controller sent and received data from the units on the System 21 bus by addressing the interface unit 7 and the switch units.

A Philips PM5139 function generator was used as the alternating-current excitation source. Tests were performed to determine the best excitation signal for the medium for in situ monitoring, to be free from distortion, accurately measured, accurately set, and reliably maintained. The system worked best with a current level between 5 and 30 mA, when measuring an object buried in soil.

Switching functions of the system were handled by six separate switch units and the interface device that connected the switch units to the buses. The interface unit was a PM2101 analog to digital converter and formed a simple communication device that resided transparently on the IEEE bus. Access to the switch units was via the GPIB address of the interface unit and the address of the function generator. The interface unit also provided power to the other units.

An optical isolation unit 11 coupled the multimeter 9, via the bus, to a personal computer 13. The personal computer received the digital signals from the multimeter and processed it using the method described below.

Generally, for imaging of objects within soil, a frequency of a few kHz was used for the signal current. At low frequencies, the analysis could proceed as a direct-current analysis. At higher frequencies, complex phasor measurements and analysis techniques are required but, otherwise, the procedure is nearly identical to the direct-current procedure. The generated current can be sine wave in form, or can be of any other effective form, such as square wave, triangular wave, etc.

In a successful embodiment, for imaging of a barrel buried in soil, the conductivity was imaged at 780 points using 38 excitation pairs and 20 electrodes.

Breast imaging should have electrodes almost surrounding the object to be imaged, thus making it easier to achieve clear results.

The computer 13 processes the signal received from the multimeter in accordance with the process described in U.S. Pat. No. 4,539,640 issued Sep. 3, 1985, invented by Bradley Fry and Alvin Wexler.

However, in accordance with one embodiment of the present invention, referred to in more detail below as the Peak Detection Method, upper and lower thresholds are applied to the values resulting from the processing at various points on the two axis (x,y) plane.

The speed of error function minimization methods can be accelerated by predicting some of the element conductivities according to differences obtained in the early stages of an image recovery procedure. The present invention determines where the prediction should be applied, by use of peak-detection. The method is initially "trained" by an approximate solution evolving soon after the method begins. Instead of checking conductivity changes for each element, this method takes the entire body as a whole and finds the areas where objects are most likely to exist. Simulation results show great improvements in the speed of convergence and quality of images in cases where adequate contrasts between the background and objects exist.

Figure 2A:
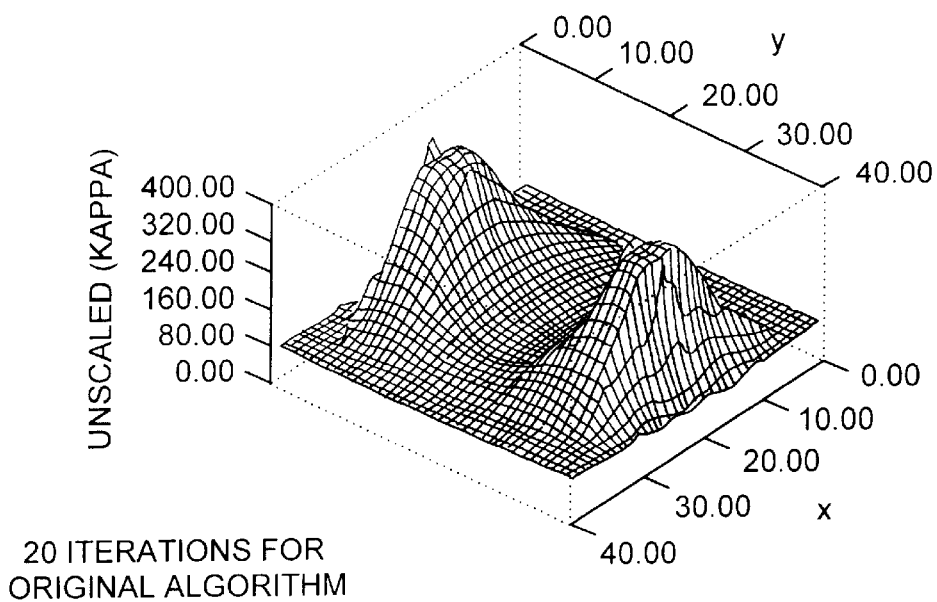
FIGS. 2A and 3A are graphs in three mutually orthogonal axes showing images of conductivity of two, and three objects respectively using a prior art method.
Figure 3A:
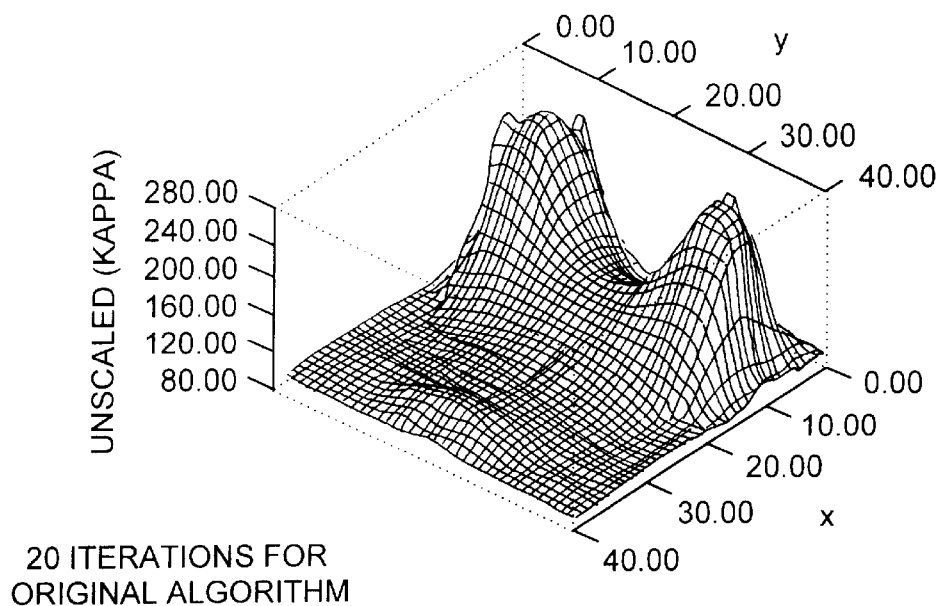

The double-constraint, error-function minimization method—on its own—does not produce an image with sharp edges in a reasonable time. What it does produce is an image with "hills" of conductivity corresponding to the location of objects, as shown in FIGS. 2A and 3A. FIGS. 2A and 3A illustrate conductivity in a plane, of a recovered image of two objects and of three objects respectively after 20 iterations using the original method. These "hills" appear regardless of whether the computation is completed for several iterations or for several hundred iterations, i.e. the conductivity improvement directions are defined at a very early stage of computation, picking the local maxima or minima and locating peaks and valleys accordingly. The method in accordance with an embodiment of the present invention modifies the derivation of images of the element conductivities with an acceleration scheme.

Figure 2B:
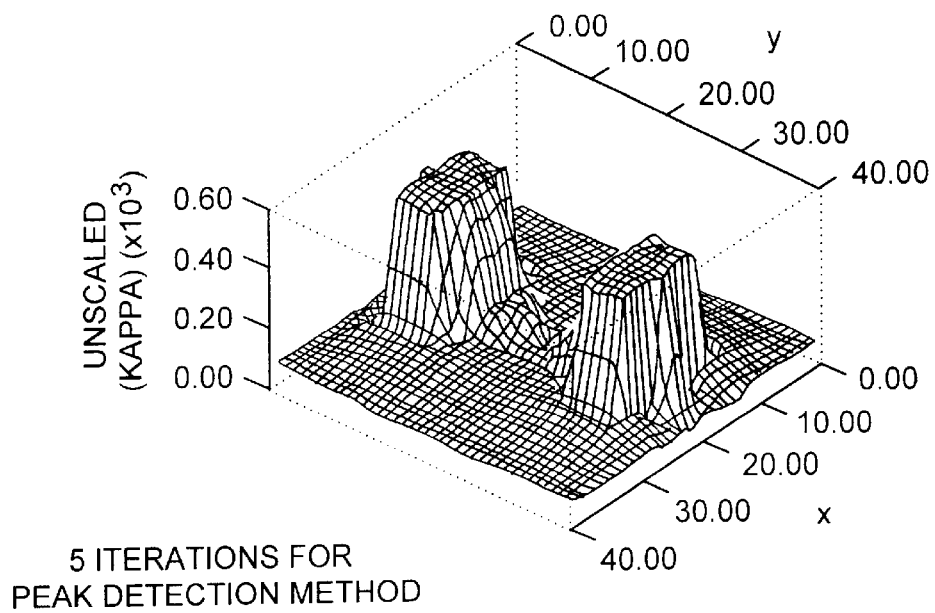
FIGS. 2B and 3B are graphs in three mutually orthogonal axes showing images of conductivity of the objects of FIGS. 2A and 3A produced in accordance with an embodiment of the present invention.
Figure 3B:
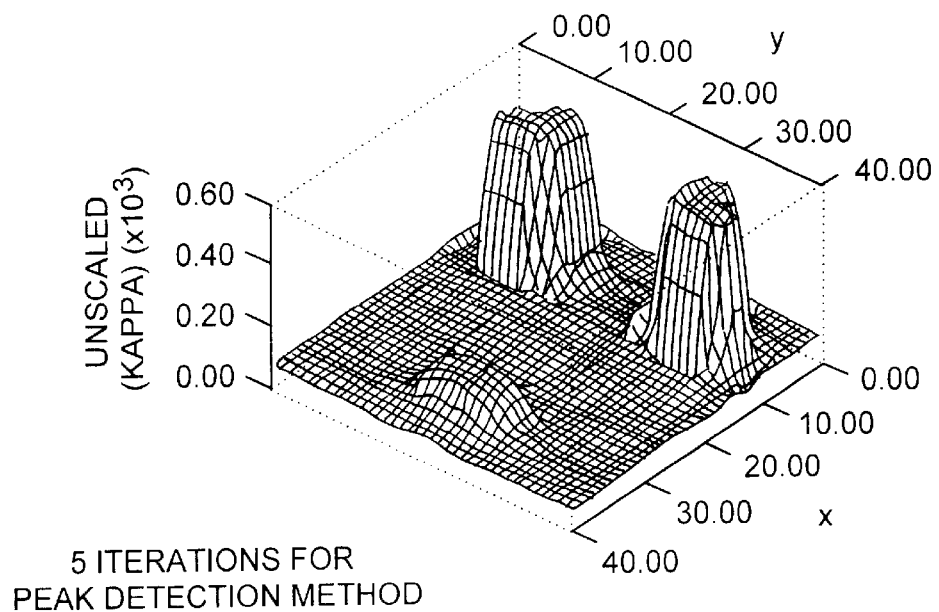

This facilitates an enormous increase in processing speed, as well as very rapid resolution, as will be noted below with reference to FIGS. 2B and 3B.

Measurement sets (described as excitations) are obtained by using pairs of electrodes as current electrodes and a selection of the remaining ones are potential measurement electrodes. Because a unique interpretation is not possible with the results of a single excitation, a number of linearly independent excitations are employed. In theory, a gradient optimization scheme, or a Newton-Raphson scheme, could be used to adjust an assumed internal conductivity distribution in order to minimize the difference between the calculated and the measured voltages over the surface. One disadvantage to these schemes is that such procedures produce dense matrices of order corresponding to the number of nodes employed. For problems with more than a few dozen nodes, this optimization procedure becomes impossibly lengthy. Fine definition cannot be achieved in this way.

Attempting to control the interior conductivity distribution from the outer surface (i.e. remotely) results in an ill-conditioned system with consequent numerical instabilities. This is akin to controlling the position of the long end of a meter stick with a fulcrum 1 cm from the short end where the finger is applied.

In accordance with the peak-detection method embodiment of the present invention, a definition of the neighbourhoods, i.e. of the "hills" and "valleys", is obtained, to which the acceleration method is applied. The boundaries are ill-defined by a straightforward application of a double-constraint, error-function minimization method. In accordance with the Peak Detection Method embodiment of the present invention, threshold criterion is utilized, between low and high-value regions, to determine boundaries within which acceleration procedures are applied. This has proven to be very successful. The result is that edges are sharpened and the regions to be detected and displayed are more clearly demarcated, as shown in FIG. 2A, which is an image obtained using the method described in the aforenoted Wexler et al. patent, and FIG. 2B, which is an image which was produced using the present embodiment after only 5 iterations. Clearly the present invention converges much faster, and to a clearer image than the aforenoted prior art method.

It should be noted that the peak-detection method is a digital image processing procedure that will sharpen images but could have the effect of causing a divergence from physical principles due to use of a strict solution of the Laplace equation. In order to avoid this effect, we use it in conjunction with a double-constraint method thus ensuring that the electromagnetic field equations are properly satisfied and that the current-flow paths are accurately determined. This permits (given that efficient methods are employed) very high definition images to be rapidly achieved. Indeed, by the use of regular finite elements, this approach can be generalized to use other object-dependent image processing methods between EIT iterations.

In operation, firstly two field solutions, one for each of the following boundary condition setups, are performed for each excitation pattern:
(a) Inhomogeneous Neumann boundary conditions are applied at each current-excitation point and homogeneous boundary conditions at points along the boundary where no electrodes are applied and with a reference ground potential applied at one or more points; and
(b) Dirichlet boundary conditions, with measured voltage values and with a reference ground potential are applied at one or more points and with inhomogeneous boundary conditions applied at each current-excitation point.

For convenience, these field solutions are termed the Neumann and Dirichlet solutions respectively. The field solutions are found through the solution of the Poisson equation:

$$-\nabla \cdot \kappa \nabla \phi = f \quad (1)$$

where $\kappa$, $\phi$ and f are the conductivity, electrical potential and impressed current source distributions respectively within the region being studied. The units are $(ohm\text{-}m)^{-1}$, volts and Amperes/$m^3$ respectively.

Although, strictly speaking, this equation holds only for the d.c. case, it is applicable to the a.c. case if the conductivity is sufficiently high so that the importance of dielectric effects is negligible. The Poisson equation is subject to the following Neumann and Dirichlet boundary conditions, which are respectively:

$$\kappa(s) \left.\frac{\partial \phi}{\partial n}\right|_s = h(s) \quad (2)$$

where (s), in Amperes/$m^2$, describes the electrical current flux density entering or leaving the medium over an electrode surface. Where no current is impressed, h(s)=0.

$$\phi(s) = g(s) \quad (3)$$

which corresponds to the measured potentials over the top surface.

Then Equation (1) is applied to each such pair of solutions for each excitation pattern. However, with boundary conditions corresponding to actual measurements and with the conductivity only an estimate of what actually existed during the measurement, the pair of boundary conditions applied to the solution cannot be expected to produce identical computed internal fields.

The imposition of Ohm's law $$\bar{J} = -\kappa \nabla \phi \quad (4)$$

where J represents the current density over the interior region employing both the previously estimated current-flow density and potential for all excitations permits a conductivity distribution to be found that yields approximate compatibility of the Neumann and Dirichlet boundary conditions to be attained. To this end, a least-square technique is employed to produce an improved estimate of the conductivity distribution—one that satisfies both boundary conditions, for all excitations, in an average sense. Thus, displacement of the conductivity estimate is caused.

With the current density (as calculated from the potential using the Neumann boundary condition throughout) and the potential (as calculated using applied voltages, i.e. the Dirichlet boundary condition where appropriate), Ohm's law is generally not satisfied. Thus, there is a residual whenever $\bar{J} + \kappa \nabla \phi$ is evaluated. To enforce compatibility, the minimization of the square of the residual over all points and for all excitations is sought. It is therefore sought to minimize $$R = \Sigma_X \iiint_V (\bar{J} + \kappa \nabla \phi) \cdot (\bar{J} + \kappa \nabla \phi) dv \quad (5)$$

where R is the squared residual sum, V is the region over which the imaging is performed, and X represents the excitations over which the sum is taken.

Several numerical methods may be used to accomplish the above operations. We have used the finite element method (FEM). In its simplest form, one may assume a constant $k_i$ value within each element i. More generally, the conductivity may be allowed to vary within each element in which case the conductivity value needs to be evaluated at several points within each element.

As an example, consider that a three-dimensional grid of nodes is defined over a cube considered to be excised from the host medium and includes the region of interest. The cube is of length l each side and is subdivided into a mesh defined by n points per edge. Thus there are n−1 links or mesh intervals to an edge, each of length $$h = l/(n-1) \quad (6)$$

Because Equation (5) can be represented as a summation over finite element volumes Vj, it can be written as $$R = \Sigma_X \iiint_V (\bar{J} + \kappa \nabla \phi) \cdot (\bar{J} + \kappa \nabla \phi) dv \quad (7)$$

where $\kappa_j$ represents the conductivity distribution within element j. For purposes of simplicity, it is here assumed that the conductivity is of constant value within each element. However, the algorithm provides for inhomogeneous conductivity values.

Then, to minimize the residual by adjustment of each conductivity $\kappa_I$, set $$\frac{\partial R}{\partial \kappa_i} = 0 \quad (8)$$

in which $\bar{J}$ and $\phi$ are held at the previously computed values. Then, upon rearranging the equation, $$\kappa_i = \frac{-\sum_X \int\int\int_{V_i} \overline{J} \cdot \nabla \phi dv}{\sum_X \int\int\int_{V_i} \nabla \phi \cdot \nabla \phi dv} \quad (9)$$

results. For each point i, the conductivity $\kappa_i$ is calculated.

The above operation yields a new conductivity value within the region of each element i. Equation (9) is applied over all points at which the conductivity $\kappa_i$ is desired. With this new set of conductivity values the operation is repeated: new field distributions are calculated using the new conductivity distribution and, consequently, a new set of conductivities is determined by Equation (9).

Figure 4A:
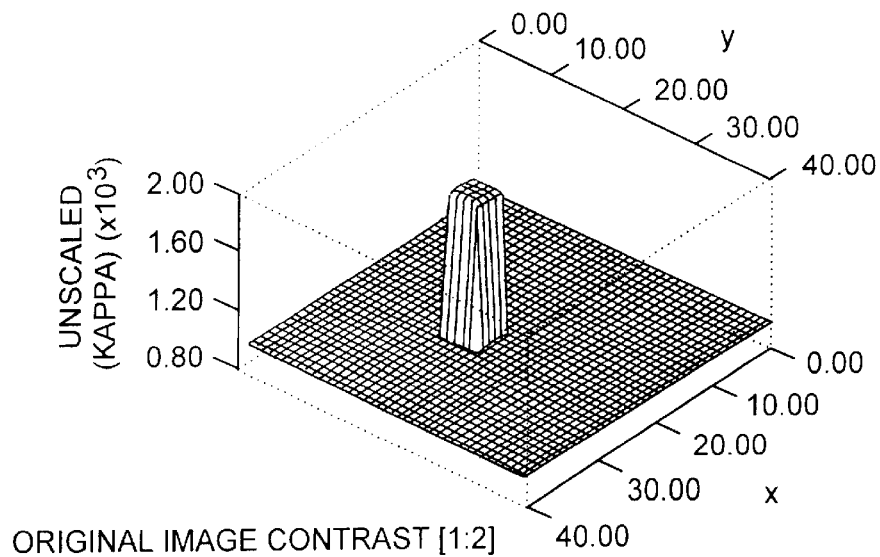
FIGS. 4A, 4B and 4C are graphs in three mutually orthogonal axes showing respectively images of conductivity of an object respectively with original image contrast, an image recovered using a prior art method, and an image recovered using the present invention with the same number of processing iterations as in the prior art method.
Figure 4B:
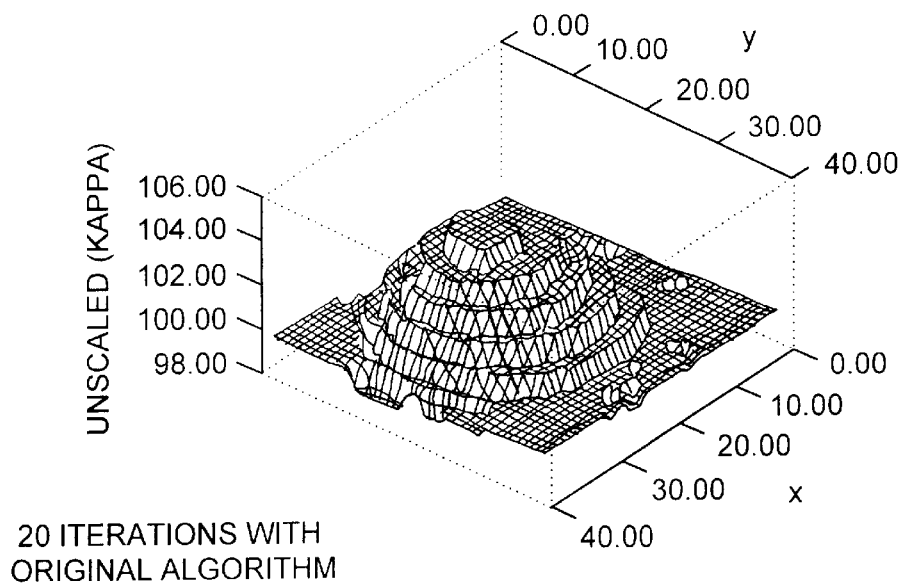
Figure 4C:
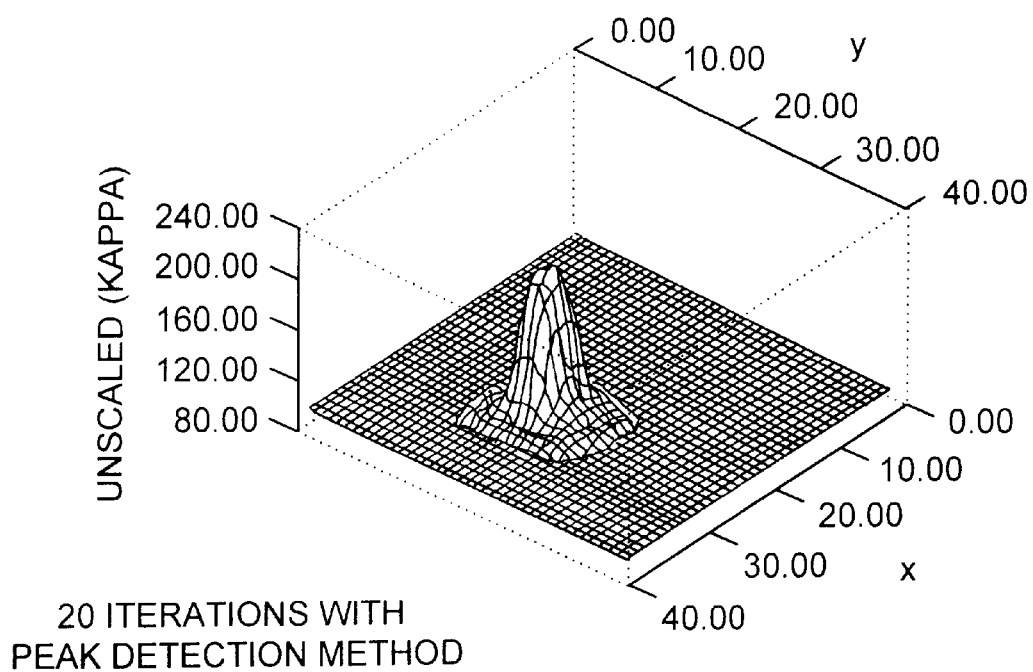

In contrast with other EIT methods, and with reference to FIGS. 4A, 4B and 4C, the prior art method described in the aforenoted Wexler et al. patent casts the problem into the interior by solving the field problem subject to the known boundary conditions (i.e. the Neumann problem with specified applied currents and the Dirichlet problem with known measured boundary potentials). This technique is referred to as the double-constraint method.

An important distinction from other inversion procedures, is that the error to be minimized (by adjustment of the conductivity distribution) is the difference between the interior current densities calculated from the Neumann and Dirichlet problems. Thus the conductivity perturbation, at any point in the interior, is controlled by field solutions near at hand rather than by long-distance. Additionally, because of the local control, the resulting matrices are sparse. This means that a great number of variables may be accommodated and the imaged object may be very well-defined. Furthermore, the error to be minimized is a squared sum over the whole region for all excitations. The process is a least-square process which carries with it a measurement-error averaging property as well as stability.

Using the above procedure, i.e. the double-constraint method of the aforenoted Wexler et al patent, a large number of iterations may be required with consequent lengthy computation times as shown in FIG. 4B. In such an iterative computation, the successive over relaxation procedure $$\omega(\kappa_i^{(n+1)} - \kappa_i^{(n)}) + \kappa_i^{(n)} \Rightarrow \kappa_i^{(n+1)} \quad (10)$$

is used to accelerate convergence of the equation solution. The iteration count is indicated by the superscript.

However, the application of Equation (10) over all of the conductivity nodes usually fails to greatly reduce the number of iterations required (i.e. a large number of potential and then conductivity iteration loops are still required) or may fail to result in convergence. It does not produce an image with sharp edges in a reasonable time.

We have now found that the successive over relaxation procedure will converge rapidly when applied specifically to regions where localized hills and valleys are found to be emerging (i.e. the Peak-Detection Method herein).

We have found that alternatively, acceleration of the process may also be induced by determining the pattern of convergence, approximating this pattern with an appropriate function, and then extrapolating the functional behaviour to the limit of an infinite number of iterations (i.e. the Multistep Extrapolation Method herein) as shown in FIG. 4C.

These methods to accelerate the imaging process are described in more detail below.

The Peak-Detection Method

Whether in two-dimensional or three-dimensional regions, a peak value of a hill (which should be construed to include the inverse of a hill) is located by scanning the data. An average value of conductivity in the surrounding region (which could include the entire remaining region) is calculated. Then, preferably, if the hill has a value greater than the surrounding terrain, a bounding surface is defined where the conductivity is, for example, 20 percent of the surrounding terrain-to-hill value above the adjacent terrain. This is treated as a threshold value. Then Equation (10) is applied only to those nodes within the hill region. Likewise, the procedure is applied to enclosed valleys.

Typically, from experience, the acceleration factor $\omega$ taken in the range 1–1.5 has yielded good results.

To sharpen the hill, once several applications of the acceleration procedure have been employed, the threshold is increased to sharpen the bounding surface locations. It has been found that a gradual increase to a 50 percent threshold value yields good results.

This has proven to be very successful. The result is that edges are sharpened and the regions are more clearly demarcated, as shown in FIGS. 2(b) and 3(b), which was produced by only 5 iterations. Clearly, the present invention resolves images much faster, and to a clearer image than the aforenoted prior art method.

Imaging in a two-dimensional region, with the peak-detection method, involves defining a region to be accelerated by a curve in the two-dimensional space. By extension, in three-dimensional space, the region would be defined by a surface in three-dimensional space. This is a direct extension.

Another three-dimensional application of the peak-detection method would be to treat the region as a sequence of two-dimensional slices and apply the methodology described for two-dimensional regions—a slice at a time.

It should be noted that the peak-detection method is a digital image processing procedure that will sharpen images but could have the adverse effect of causing a divergence from physical principles by use of the strict solution of the Laplace/Poisson equation. In order to avoid this effect, it is preferred that it should be used in conjunction with the double-constraint method thus ensuring that the electromagnetic field equations are properly satisfied and that the current-flow paths are accurately determined. This permits (given that efficient field-solving methods are employed) very high definition images to be achieved. Indeed, by the use of regular finite element methods, this approach can be generalized to use any of several object-dependent image processing methods between EIT iterations.

The Multistep Extrapolation Method

In accordance with another embodiment, the displacements of the conductivity value at each conductivity-calculation stage is tracked. The displacement value, at each node at which the conductivity is calculated, is evaluated. Then, a number of functions are examined to find the one (called the characteristic equation) that best describes the behaviour of the displacement norm as a function of iteration count. We have found the following equation to describe very well the behaviour of the converging pattern (and, likely, others may be used as alternatives of the conductivity (or specific impedance, generally) convergence behaviour:

$$a_0 + a_1/\sqrt{(n)} + a_2/(n)^{3/2} + a_3 \log(n)/n^2 \quad (11)$$

where n is the iteration count. The coefficients are determined by fitting this (or another) equation to the data. Then $a_0$ is the ultimate conductivity value. This results in quick convergence to the images such as those shown in FIGS. 3B and 4C, as contrasted with the images such as those shown in FIGS. 3A and 4B.

Figure 5:
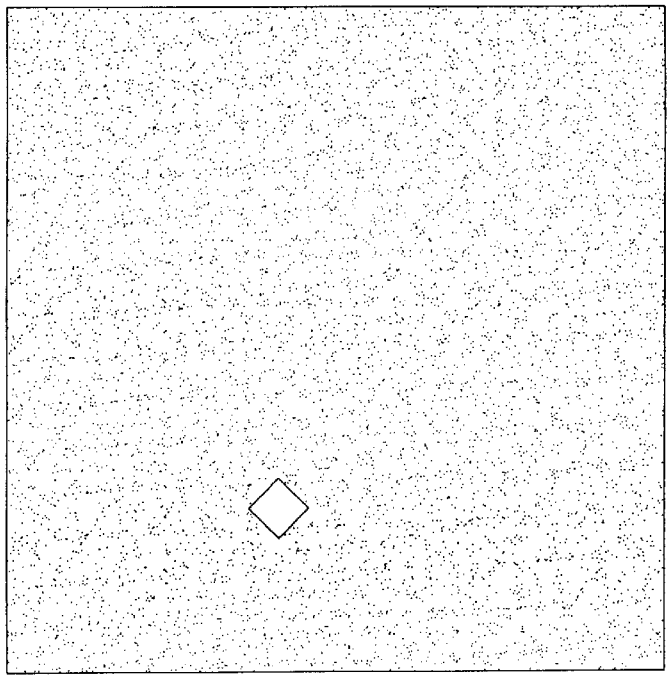
FIG. 5 illustrates a model object, of a resulting image, using the method of the present invention, FIG. 6 are graphs of error function using prior art method and of the present invention, showing how quickly the present invention converges.
Figure 5:
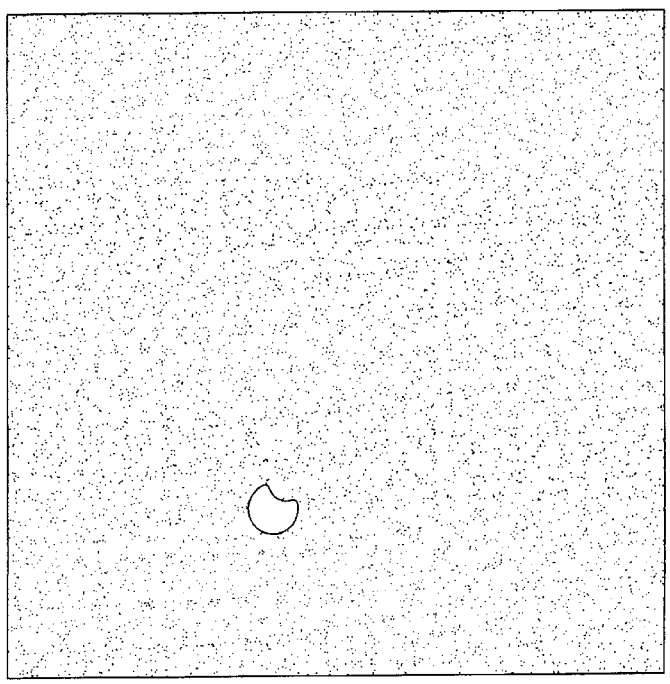

FIG. 5 illustrates a model object, and of a resulting image, using the method of the present embodiment.

Figure 6:
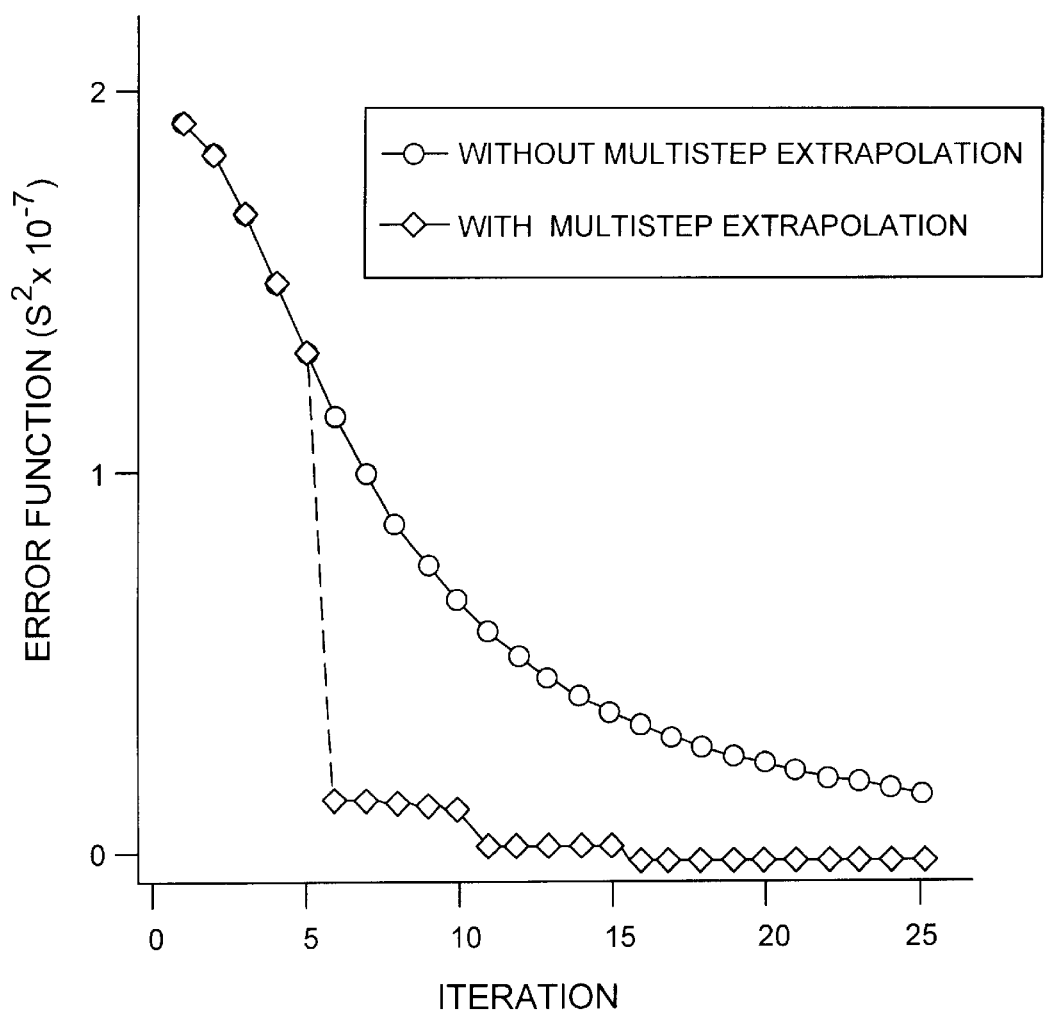

The speed of convergence is also clear from the graphs shown in FIG. 6, which shows an error function according to the prior art, without the multistep extrapolation method, and with the multistep extrapolation in accordance with the present invention.

Figure 7A:
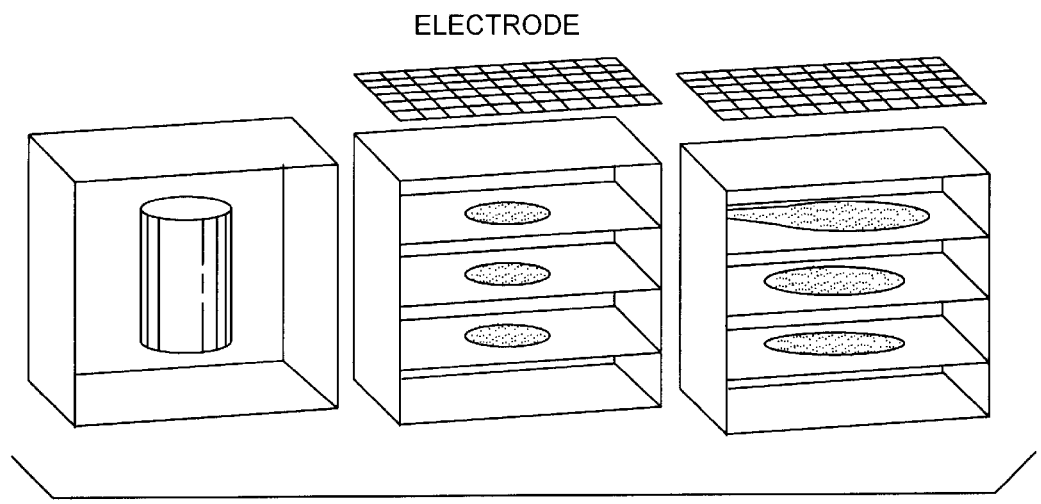
FIGS. 7A and 7B show recovered images using an embodiment of the present invention for a steel barrel buried within sandy soil.
Figure 7B:
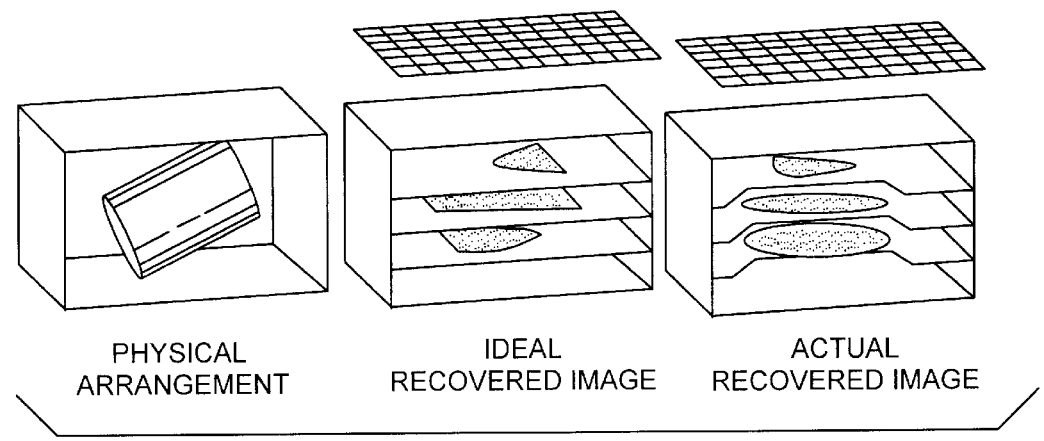

FIGS. 7A and 7B show recovered images for a steel barrel buried within sandy soil. Two orientations of the barrel were employed and an indication of this is provided by the experimental results obtained. FIG. 7A shows a vertical barrel and FIG. 7B shows a tilted barrel. The left image in each of these figures is of the physical arrangements, the center image of these figures show the ideal recovered image, and the right image of these figures are obtained from operation of the method of this invention.

All excitations and measurements were restricted to the top surface of the soil. The current measurements were taken and the data was stored in the personal computer. The imaging method was performed and the graphics were presented by a Silicon Graphics workstation. The image processing was accomplished by the double-constraint method described in the prior art and produced the presented images in 650 iterations. Using the double-constraint method augmented by the peak-detection and the multistep extrapolation methods in accordance with the present invention, the convergence curve indicated convergence in only 5 to 10 iterations. The required convergence count reduction is about two orders of magnitude, thus greatly enhancing the usability of the system.

A person understanding this invention may now conceive of alternative structures and embodiments or variations of the above. All those which fall within the scope of the claims appended hereto are considered to be part of the present invention.

We claim:

1. A method of electrical impedance tomography imaging of an object contained in a medium, having a specific impedance which is different from the specific impedance of the medium, comprising;

(a) applying current to the medium at first predetermined locations at a surface of the medium, (b) extracting current at second predetermined locations, (c) detecting voltages produced by the current which has passed through the medium from the surface of the medium at said second locations, (d) successively determining a location and shape and conductivity of the object with increasing accuracy by processing values of the detected voltages, (e) determining a region in the medium in which the object is located from values of the detected voltages which are within upper and lower threshold values, (f) applying a successive over relaxation acceleration procedure to the conductivities determined within the region in the course of repetitive iterative refinement of these values in the course of said imaging procedure, (g) subsequently restricting further determination of the location of the object with increasing accuracy to voltages obtained from said region of the medium in which the object is located, (h) and displaying an image of said object using the restricted location determination values.

2. A method as defined in claim 1 including determining and displaying two dimensional image slices of adjacent portions of the medium so as to form a three dimensional image of the object in the medium.

\* \* \* \* \*